US008367397B2

(12) United States Patent
Gu et al.

(10) Patent No.: US 8,367,397 B2
(45) Date of Patent: Feb. 5, 2013

(54) ACTIVE BIOCHIP FOR NUCLEIC ACID ANALYSIS

(75) Inventors: Yuandong Gu, Plymouth, MN (US); Leon Xu, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 992 days.

(21) Appl. No.: 11/706,507

(22) Filed: Feb. 15, 2007

(65) Prior Publication Data

US 2008/0199862 A1 Aug. 21, 2008

(51) Int. Cl.
*C12M 1/00* (2006.01)

(52) U.S. Cl. .................................................... 435/283.1

(58) Field of Classification Search ........................ None
See application file for complete search history.

(56) References Cited

U.S. PATENT DOCUMENTS 6,111,096 A 8/2000 Laugharn et al.
6,168,948 B1 * 1/2001 Anderson et al. .......... 435/287.2
6,375,901 B1 * 4/2002 Robotti et al. ................ 422/103
6,561,208 B1 * 5/2003 O'Connor et al. ......... 137/15.18
2005/0232817 A1 * 10/2005 Ahn et al. ....................... 422/99

FOREIGN PATENT DOCUMENTS

WO WO 9933559 A1 * 7/1999
WO WO-9933599 A1 7/1999
WO WO-0178893 A2 10/2001
WO WO 0178893 A2 * 10/2001
WO WO-2006038159 A1 4/2006

OTHER PUBLICATIONS

"International Application Serial No. PCT/US2008/053911, International Search Report and Written Opinion mailed Jul. 23, 2008".
Ahn, C. H., et al., "Disposable smart lab on a chip for point-of-care clinical diagnostics", *Proceedings of the IEEE*, 92(1), (2004), 154-173.
Hong, C. C., et al., "A functional on-chip pressure generator using solid chemical propellant for disposable lab-on-a-chip.", *Lab Chip.*, 3(4), (2003), 281-6.
Markov, G. G., et al., "Hydroxyapatite column chromatography in procedures for isolation of purified DNA", *Anal Biochem.*, 59(2), (1974), 555-63.
Qiu, Y., et al., "Environment-sensitive hydrogels for drug delivery", *Advanced Drug Delivery Reviews*, 53(3) , (2002), 321-339.

* cited by examiner

*Primary Examiner* — Christopher M. Babic
(74) *Attorney, Agent, or Firm* — Schwegman, Lundberg & Woessner, P.A.

(57) ABSTRACT

Embodiments of the invention relate to an active biochip for nucleic acid analysis. The biochip comprises an inlet for introducing a nucleic acid sample, fluid channels, valves in contact with the fluid channels and pumps in contact with the fluid channels and adapted to generate a carrier gas or move a buffer through a portion of the fluid channels. The biochip also includes one or more hydroxyapatite columns for separating a portion of the nucleic acid sample, buffer reservoirs in contact with the fluid channels and positioned near the pumps, air exits, a waste reservoir and a nucleic acid analysis region.

18 Claims, 4 Drawing Sheets

ACTIVE BIOCHIP FOR NUCLEIC ACID ANALYSIS

TECHNICAL FIELD

Embodiments of the present invention relate to an active biochip for nucleic acid preparation. More specifically, embodiments of the invention relate to an active biochip for DNA analysis utilizing a hydroxyapatite chromatographic adsorption column.

BACKGROUND

Nucleic acid diagnosis is an important and blooming part of in vitro diagnosis (IVD), in which polymerase chain reaction (PCR) and other nucleic acid amplification techniques are the principal diagnosis tool. Nucleic acid (e.g., DNA) microarrays are currently being explored as an interesting technology platform for future IVD products. However, there are still technological bottlenecks to be resolved in the nucleic acid testing process. These problems hinder the goal for making the analysis more simple, robust, rapid and reproducible. Sample handling represents one of the main bottlenecks. It usually takes more than one man-hour to prepare a dozen nucleic acid samples from clinical samples. Another challenge to a medical lab is to process the thousands of samples waiting for nucleic acid preparation on a daily basis. More importantly, heavy sample preparation work will often induce cross-contamination and false positive or false negative results. This causes a low reproducibility and high variation in the testing.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

SUMMARY

Figure 1:
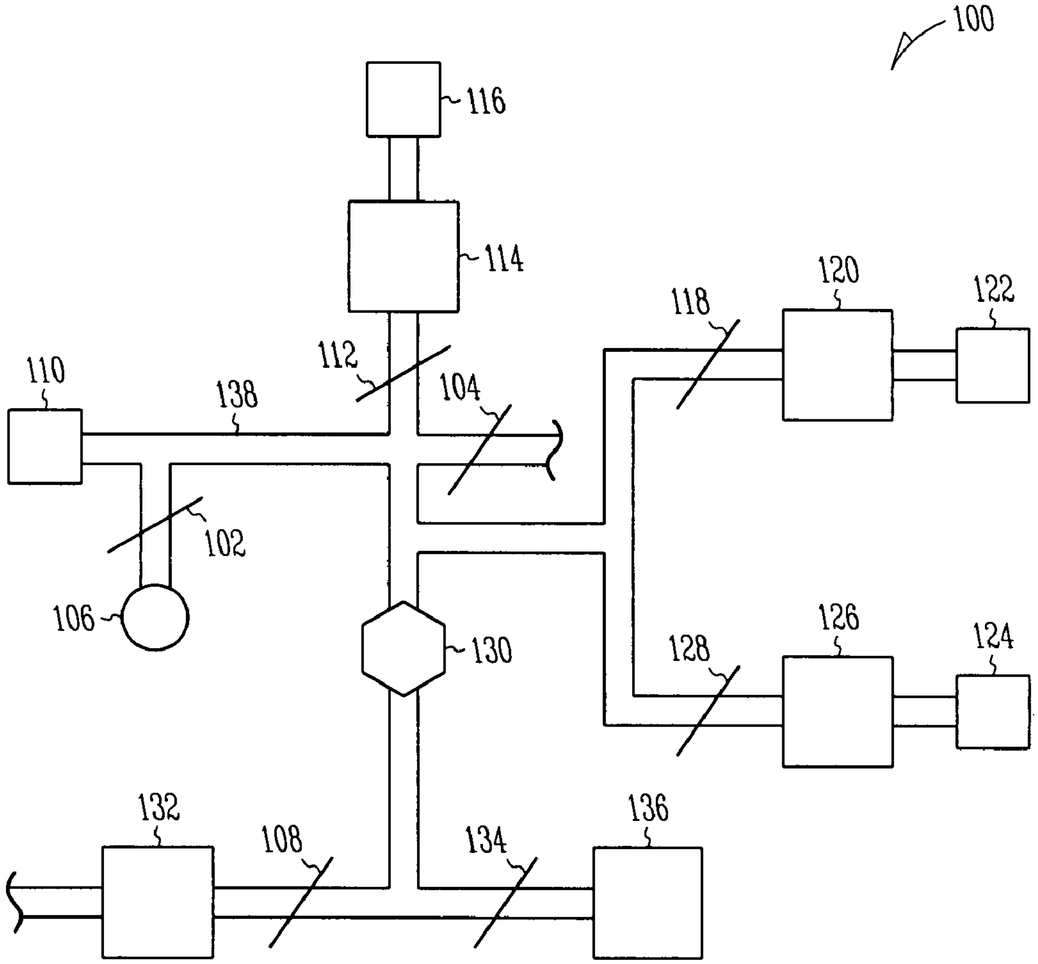
FIG. 1 illustrates a schematic view of an active biochip for nucleic acid preparation 100, according to some embodiments.

Embodiments of the invention relate to an active biochip for nucleic acid analysis. The biochip comprises an inlet for introducing a nucleic acid sample, fluid channels, valves in contact with the fluid channels and pumps in contact with the fluid channels and adapted to generate a carrier gas or move a buffer through a portion of the fluid channels. The biochip also includes one or more hydroxyapatite columns for separating a portion of the nucleic acid sample, buffer reservoirs in contact with the fluid channels and positioned near the pumps, air exits, a waste reservoir and a nucleic acid analysis region.

Embodiments of the present invention also relate to a method of analyzing a nucleic acid sample utilizing an active biochip. The method comprises introducing a nucleic acid sample to a fluid channel in the biochip, activating a carrier gas sufficient to move the nucleic acid sample through the fluid channel, binding at least a portion of the sample on a hydroxyapatite column, removing unspecific binding substances from the column, releasing the bound portion of the sample sufficient to provide a released sample and analyzing the released sample.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Embodiments of the invention relate to an active biochip for nucleic acid preparation. The biochip allows for a simple, robust, rapid and reproducible nucleic acid testing system. The biochip utilizes hydroxyapatite (HA) chromatographic absorption for nucleic acid preparation that is capable of preparing pure nucleic acid in an automated fashion for PCR and microarray analysis. Because hydroxyapatite is a biocompatible material capable of specific binding with nucleic acid in a high salt condition, it can be integrated into a microfluidic biochip for purification of nucleic acid. The active microfluidic biochip is laborsaving and whole-sealed, which reduces the operative error and cross-contamination and increases the reliability of the analytical results. The nucleic acid sample preparation/analysis may be automated and completed in around 10 minutes, rather than hours.

Referring to FIG. 1, a schematic view of an active biochip for nucleic acid preparation 100 is shown, according to some embodiments. An inlet 106 may be connected to fluid channel 138. The inlet 106 may be an injection port, for example. A first valve 102 may be positioned in the fluid channel 138 near the inlet 106. A first pump 110 may be positioned near valve 102 and inlet 106. A second pump 116 may be positioned adjacent to a low salt buffer reservoir 114. A second valve 112 may be positioned in the fluid channel 138 adjacent to the low salt buffer reservoir 114. Third valve 118 and fourth valve 128 may be positioned adjacent to high salt buffer reservoirs 120 and 126 respectively. Third pump 122 and fourth pump 124 may similarly be positioned adjacent to high salt buffer reservoirs 120 and 126 respectively. A hydroxyapatite chromatographic adsorption column 130 may be positioned in fluid channel 138. Fifth valve 108 may be positioned in the fluid channel 138 adjacent to waste reservoir 132. Sixth valve 134 may be positioned adjacent to nucleic acid analysis region 136. A seventh valve 104 may also be positioned in the fluid channel 138.

First valve 102 and seventh valve 104 may be in an open position when introducing a sample that contains a nucleic acid into the inlet 106. Valves 102 and 104 may then be closed and the fifth valve 108 may be opened. Pump 110 may then be activated, such as by heating to generate a carrier gas. The sample may then be pushed through the HA column 130 and into the waste reservoir 132. The target nucleic acid will selectively bind to the column 130. Pump 110 may then be stopped and the third pump 122 activated (valve 118 now open). Pump 122 will then push a high salt buffer (from reservoir 120) through the column 130 to wash any unspecific binding substance from the column to the waste reservoir 130. Pump 122 may then be stopped and then the washing may be repeated with pump 134, while opening valve 128. Valves 118, 128 and 108 may be closed and valves 112 and 134 opened. Pump 116 may then be activated to push a low salt buffer from reservoir 114 through the column 130, which releases the bound target nucleic acids in the sample. The released sample then flows to the nucleic acid analysis region 136. The valves, heaters, pumps and analysis region may all be controlled by on-board chip circuitry.

Figure 2:
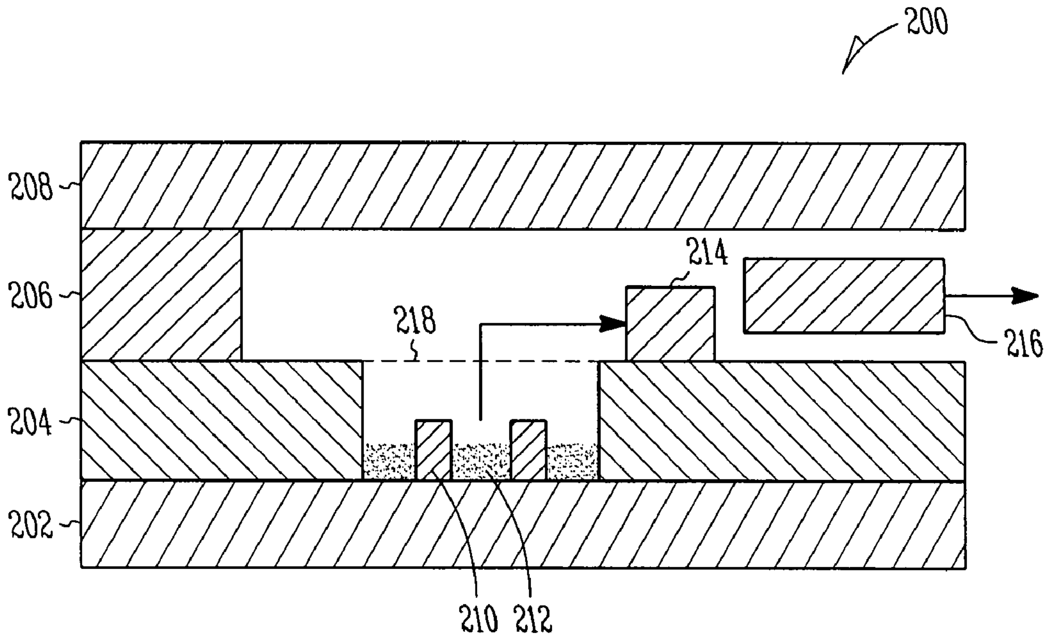
FIG. 2 illustrates a cross-sectional view of a microfluidic pump 200 utilized in an active biochip, according to some embodiments.
Figure 3:
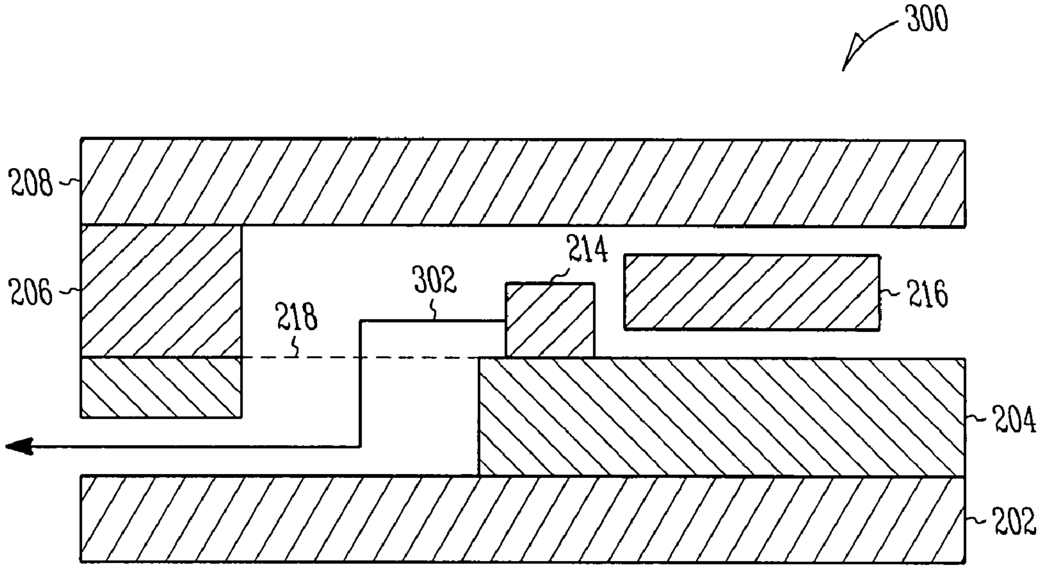
FIG. 3 illustrates a cross-sectional view of an air exit 300 utilized in an active biochip, according to some embodiments.

Referring to FIG. 2, a cross-sectional view of a microfluidic pump 200 utilized in an active biochip is shown, according to some embodiments. A first layer 202 comprises an electrocircuit layer which may be embedded with circuits to control heating, cooling and any sensing of the fluid. The second layer 204 may contain channels and windows, for example. A solid chemical propellant 212 may be in contact with heating elements 210. A porous polymer film 218 may cover the solid chemical propellant 212 and heating elements 210. The third layer 206 may include further channels for fluid moving and buffer storage. A reflux preventor 214 may be positioned between fluid 216 and the solid chemical propellant 212. The reflux preventor 214 prevents solution from entering the pump. A fourth layer 208 may be utilized to cover and seal the biochip. An air exit 300 (FIG. 3) may be utilized in conjunction with the pump 200, allowing an exit gas flow 302 in the channel. The air exit 300 maintains a stable pressure in the channel. As the propellant 212 expands and pushes the fluid through the channel, pressure builds up. The air exit 300 dissipates the pressure build-up.

The solid chemical propellant 212 may include azobisisobutyronitrile (AIBN), for example. The propellant 212 may be in powder form. The solid chemical propellant 212 may be heated to produce a gas, such as nitrogen. The output pressure of the gas, generated from the solid chemical propellant, may be adjustable to a desired pressure by controlling the input power of the heater. The gas may be utilized as a carrier gas to push a fluid sample through the fluid channel.

The layers 202, 204, 206 and 208 may be manufactured of an inexpensive plastic, such as polymethyl methacrylate (PMMA) or polydimethylsiloxane (PDMS), for example. The second 204 and third layers 206 may be crosslinked in certain areas, to support porous membranes or channel structure, for example. The four layers may be bonded by plastic hot embossing processes.

Figure 4A:
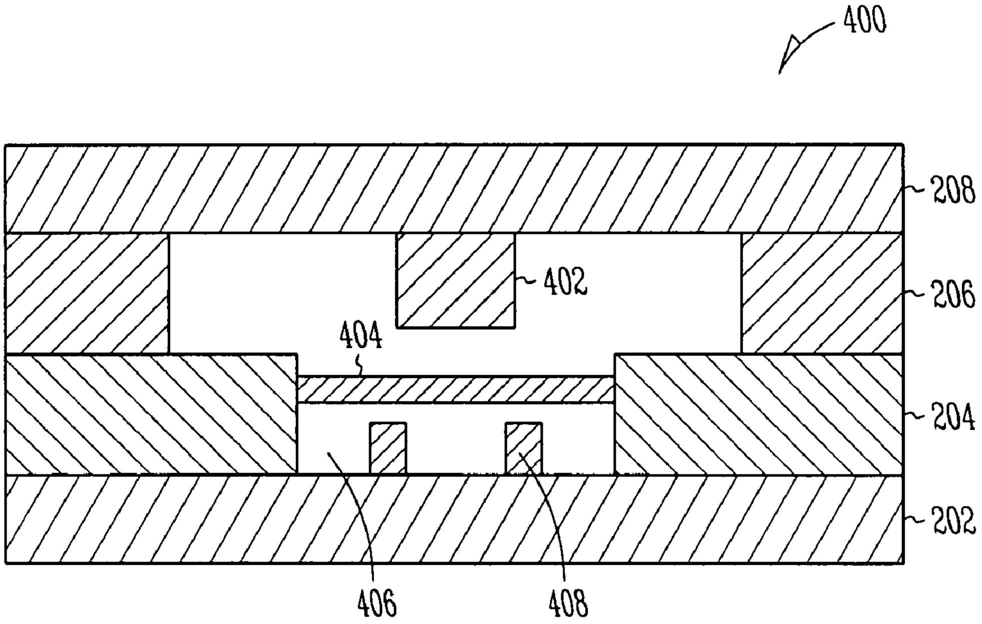
FIGS. 4A-B illustrates cross-sectional views of a valve 400 utilized in an active biochip, according to some embodiments.
Figure 4B:
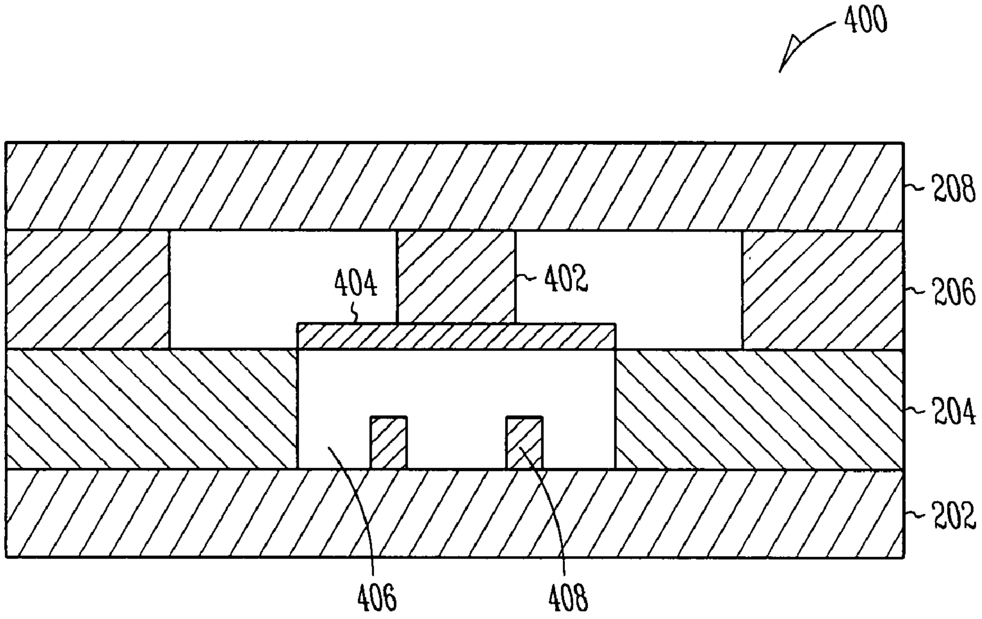

Referring to FIGS. 4A-B, cross-sectional views of a valve 400 utilized in an active biochip is shown, according to some embodiments. A valve 400 may include a hydrogel 406 and in contact with one or more electrodes or heating elements 408. The hydrogel 406 may be enclosed by an elastic and waterproof polymer 404 on a least one side. In an open position (FIG. 4A), fluid may pass through the channel around structure 402. When heated or exposed to electrical current, the hydrogel 406 will expand and contact the structure 402, effectively blocking the channel (FIG. 4B).

A hydrogel is a network of hydrophilic polymers that can swell in water and hold a large amount of water while maintaining their structure. A three-dimensional network is formed by cross-linking polymer chains. The hydrogel 406 utilized as a valve may be temperature sensitive. Examples of such hydrogels include poly(N-iso-propylacrylamide) (PNIPAAm) and poly(N,N-diethylacrylamide) (PDEAAm), for example.

Figure 5:
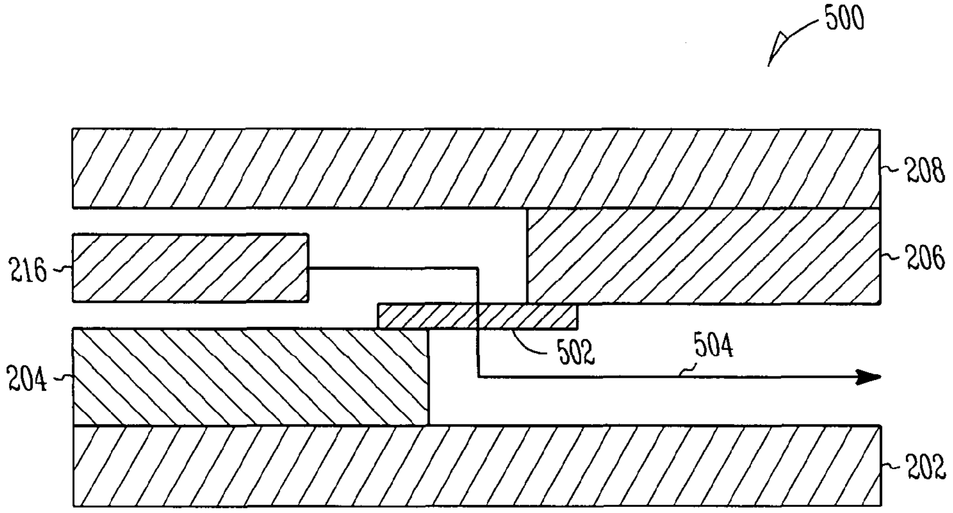
FIG. 5 illustrates a cross-sectional view of a hydroxyapatite chromatographic adsorption column 500 utilized in an active biochip, according to some embodiments.

Referring to FIG. 5, a cross-sectional view of a hydroxyapatite chromatographic adsorption column 500 utilized in an active biochip is shown, according to some embodiments. Hydroxyapatite material 502 may be placed in the fluid path 504. As the fluid 216 passes through the channel, the target sample may selectively bind to the column 500. Double-stranded DNA has a much higher affinity to hydroxyapatite than RNA, proteins, carbohydrates and various low molecular weight substances. This allows the isolation of DNA, free of contaminants, by contacting a nucleic acid sample to the column and then eluting with buffers of appropriate concentrations.

Figure 6:
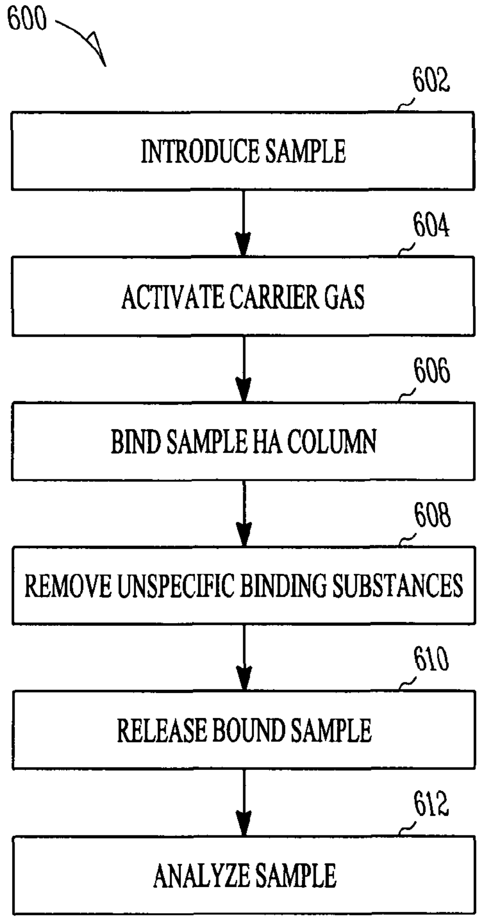
FIG. 6 illustrates a block flow diagram of a method of analyzing a nucleic acid sample 600 utilizing an active biochip, according to some embodiments.

Referring to FIG. 6, a block flow diagram of a method of analyzing a nucleic acid sample 600 utilizing an active biochip is shown, according to some embodiments. A nucleic acid sample may be introduced 602. A carrier gas may then be activated 604 to move the sample to an HA column, where the target nucleic acid sample may be bound 606. Unspecific binding substances may be removed 608 from the sample, such as by washing. Washing may be repeated two or more times. The bound sample may be released 610, such as by contacting with a low salt buffer. The sample may then move to a nucleic acid analysis region, where the sample is analyzed 612.

The sample may be lysed tissue, for example. The sample may be introduced 602 by injection. The carrier gas may be activated 604 by heating a solid chemical propellant to generate the carrier gas. The unspecific binding substances may be removed 608 from the column by contacting with a high salt buffer, such as by washing. Releasing 610 the bound sample may include contacting the sample with a low salt buffer. The nucleic acid analysis region may include a microarray or a PCR region in conjunction with a microarray, for example. The sample may be analyzed 612 by amplification or by microarray detection methods.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:

1. An active biochip for nucleic acid analysis, the biochip comprising:

a nucleic acid sample;

an inlet, for introducing the nucleic acid sample;

one or more fluid channels;

two or more valves, comprising hydrogels enclosed by an elastic and waterproof polymer in contact with the fluid channels;

two or more pumps, in contact with the fluid channels and adapted to generate a carrier gas;

one or more hydroxyapatite columns, for separating a portion of the nucleic acid sample;

one or more high salt buffer reservoirs containing one or more high salt buffers, in contact with the one or more fluid channels and positioned adjacent to at least one pump;

one or more low salt buffer reservoirs containing one or more low salt buffers, in contact with the one or more fluid channels and positioned adjacent to at least one pump;

one or more air exits, positioned within or adjacent at least one pump and adapted to relieve gas pressure buildup;

a waste reservoir; and a nucleic acid analysis region wherein the biochip is a microfluidic biochip and whole-sealed.

2. The biochip of claim 1, wherein the inlet comprises an injection port.

3. The biochip of claim 1, wherein the nucleic acid sample is DNA.

4. The biochip of claim 1, wherein the valves comprise poly(N-iso-propylacrylamide) (PNIPAAm).

5. The biochip of claim 1, wherein the valves comprise poly(N,N-diethylacrylamide) (PDEAAm).

6. The biochip of claim 1, wherein the pumps comprise a solid chemical propellant.

7. The biochip of claim 1, wherein the pumps comprise azobis-isobutyronitrile (AIBN).

8. The biochip of claim 1, wherein the nucleic acid analysis region comprises one or more of a microarray and a nucleic acid amplification region.

9. The biochip of claim 8, wherein the nucleic acid amplification region comprises a polymerase chain reaction (PCR) region.

10. A method of analyzing a nucleic acid sample utilizing an active microfluidic biochip, the method comprising:

introducing a nucleic acid sample to a fluid channel in the active microfluidic biochip of claim 1;

activating a carrier gas, sufficient to move the nucleic acid sample through the fluid channel;

binding at least a portion of the sample on a hydroxyapatite column;

removing unspecific binding substances from the column;

releasing the bound portion of the sample, sufficient to provide a released sample; and analyzing the released sample.

11. The method of claim 10, wherein introducing comprises injecting.

12. The method of claim 10, wherein activating comprises heating a solid chemical propellant sufficient to generate the carrier gas.

13. The method of claim 10, wherein removing comprises contacting with a high salt buffer.

14. The method of claim 10, wherein releasing comprises contacting with a low salt buffer.

15. The method of claim 10, wherein analyzing comprises analyzing a microarray.

16. The method of claim 10, wherein analyzing comprises analyzing nucleic acid amplification.

17. The method of claim 10, wherein analyzing comprises analyzing PCR.

18. An active biochip for nucleic acid analysis, the biochip comprising:

a nucleic acid sample;

an inlet, for introducing the nucleic acid sample;

one or more fluid channels;

two or more valves, comprising hydrogels enclosed by an elastic and waterproof polymer in contact with the fluid channels;

two or more pumps;

one or more hydroxyapatite columns, for separating a portion of the nucleic acid sample;

one or more high salt buffer reservoirs containing one or more high salt buffers, in contact with the one or more fluid channels and positioned adjacent to at least one pump;

one or more low salt buffer reservoirs containing one or more low salt buffers, in contact with the one or more fluid channels and positioned adjacent to at least one pump;

one or more air exits, positioned adjacent to or within at least one pump and adapted to relieve gas pressure buildup;

a waste reservoir; and a nucleic acid analysis region;

wherein the two or more pumps include a solid propellant and upon heating, generate a carrier gas capable of moving the sample or one or more buffers through the one or more fluid channels; and wherein the two or more pumps include a reflux preventor positioned between the solid propellant and sample or one or more buffers wherein the biochip is a microfluidic biochip and whole-sealed.

* * * * *